United States Patent [19]
Angelchik

[11] 4,271,828
[45] Jun. 9, 1981

[54] METHOD FOR MAINTAINING THE REDUCTION OF A SLIDING ESOPHAGEAL HIATAL HERNIA

[76] Inventor: Jean P. Angelchik, 1728 W. Glendale Ave., Suite 401, Phoenix, Ariz. 85021

[21] Appl. No.: 75,271

[22] Filed: Sep. 13, 1979

[51] Int. Cl.³ .......................... A61B 19/00; A61F 1/00
[52] U.S. Cl. .................................................. 128/1 R
[58] Field of Search ................... 3/1; 128/1 R, 334 R, 128/325, 95, 346, 96, DIG. 23, DIG. 25

[56] References Cited
U.S. PATENT DOCUMENTS
3,875,928   4/1975   Angelchik .......................... 128/1 R

*Primary Examiner*—Frank A. Spear, Jr.
*Attorney, Agent, or Firm*—Drummond and Nelson

[57] ABSTRACT

A method for maintaining the intra-abdominal reduction of a sliding esophageal hernia. The method comprises positioning a generally C-shaped cushion prosthesis around the distal esophagus between the diaphragm and stomach. The overall size of the prosthesis is large enough to prevent extension of the gastric fundus into the thoracic cavity through an enlarged esophageal hiatus. The prosthesis is of generally constant cross-sectional area along its entire length to prevent upward migration of the prosthesis through the enlarged esophageal hiatus and to maintain the accentuated curvature of the esophagus induced by emplacement of the prosthesis. Tie means are provided to maintain the prosthesis in operative position.

1 Claim, 5 Drawing Figures

METHOD FOR MAINTAINING THE REDUCTION OF A SLIDING ESOPHAGEAL HIATAL HERNIA

This invention relates to methods for using a surgical prosthesis.

More particularly, the invention concerns an improved method for using a surgical prosthesis to maintain the intraabdominal reduction of a sliding esophageal distal hernia.

When the esophageal hiatus of the diaphragm muscle becomes enlarged, a portion of the stomach immediately below the gastro esophageal junction (the gastric fundus) may actually slide upwardly through the esophageal hiatus into the chest or thoracic cavity. This anatomical condition, known as a "sliding esophageal hernia" frequently causes gastro esophageal reflux in which stomach acids and food are regurgitated into the esophagus.

Various procedures have been devised for the repair of sliding esophageal hernias. In this regard, my earlier issued U.S. Pat. No. 3,875,928 discloses a method for maintaining the reduction of a sliding esophageal hiatal hernia. The method comprises emplacing a C-shaped prosthesis about the distal esophagus between the gastric fundus and the diaphragm. The prosthesis has a tape secured about the periphery thereof. The free ends of the tape, which extend well beyond the tapered ends of the C-shaped cushion, are tied together and sutured to the stomach to maintain the prosthesis in proper operative position.

As illustrated in FIG. 6 of my earlier issued patent, when the prosthesis is in the proper operative position, the larger diameter central portion of the C-shaped cushion bears against the hind side of the esophagus 17 and accentuates the curvature which exists in the portion of the esophagus between the stomach 43 and diaphragm 13. This increased curvature in the esophagus 17 apparently minimizes the probability of recurrence of gastro esophageal reflux and also makes upward migration of the prosthesis and upper portion of the stomach 45 through the hiatal hernia more difficult.

Observation has confirmed that the repetitive contracting movements of the stomach 43 cause the sutures attaching free ends 27 to the stomach 43 to be of transient nature. When the sutures free themselves from the wall of the stomach 43, the prosthesis 20 tends to rotate about the esophagus 17 and the tapered ends 23 move behind the distal esophagus 17 and above the upper part of the stomach 45. When the tapered ends 23 have rotated to a position behind the esophagus 17, outward pressure on the esophagus 17 is largely diminished. As a result, the additional curvature originally imparted to the esophagus by the greater sized center portion of the prosthesis is lost, and the recurrence of gastro esophageal reflux is more probable.

In addition, after rotating to a position above the upper part of the stomach 45, the tapered ends 23 typically move upwardly into and through the enlarged esophageal hiatus 12 such that the prosthesis 20 migrates from the desired operative position to a position above the diaphragm 13.

Alternatively, when the sutures disengage from the stomach 43, the prosthesis 20 may, without rotating, simply travel essentially vertically up the esophagus 17 allowing the tapered ends 23 to move into the enlarged esophageal hiatus 12 and promote migration of the prosthesis from the proper operative position to a position above the diaphragm 13.

Accordingly, it is the principle objective of the present invention to provide an improved method for maintaining the intra-abdominal reduction of a sliding esophageal distal hernia.

Another objective of the invention is to provide an improved method for positioning a surgical prosthesis about the distal esophagus which can maintain the prosthesis in the desired position between the diaphragm and stomach.

Yet another objective of the invention is to provide an improved method for emplacing a prosthesis about the distal esophagus which would maintain the accentuated curvature of the portion of esophagus between the stomach and diaphragm and which would not necessitate suturing the prosthesis to the stomach or to other anatomical structures.

These and other further and more specific objectives and advantages of the invention will be apparent to those skilled in the art from the following detailed description thereof, taken in conjunction with the drawings in which.

Briefly, in accordance with my invention I provide an improved method for maintaining the intra-abdominal reduction of a sliding esophageal hiatal hernia whereby extension of the gastric fundus into the thoracic cavity through an enlarged esophageal hiatus is prevented. The improved method comprises positioning a generally C-shaped cushion prosthesis around the distal esophagus, adjusting the free ends of the prosthesis at a spacing to permit normal expansion of the esophagus during swallowing, and fixing the free ends of the prosthesis in the adjusted position to maintain the C-shaped cushion prosthesis in operative position around the distal esophagus between the gastric fundus and the diaphragm and to maintain the adjusted spacing of the free ends. The C-shaped cushion is deformable to permit adjustment of the spacing of the free ends thereof at a selected distance and has a generally constant cross-sectional area along the length thereof. The inside diameter of the prosthesis generally corresponds to the normal outside diameter of the distal esophagus and the outside diameter thereof is larger than the enlarged esophageal hiatus.

The prosthesis employed in my improved method bears radiopaque indicia which facilitate radiograph determination of the position of the prosthesis after emplacement thereof around the distal esophagus.

Figure 1:
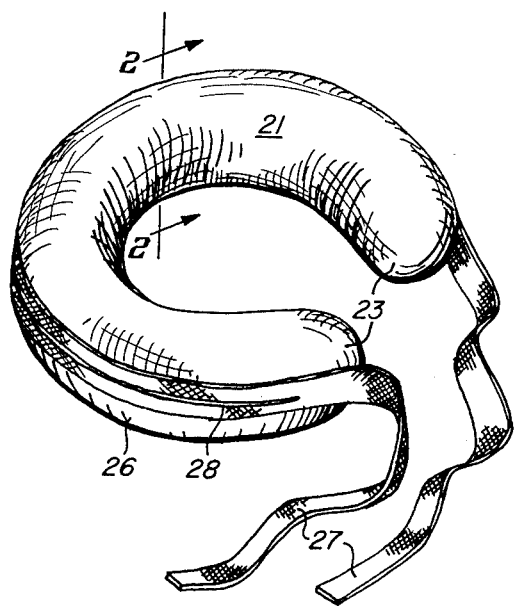
FIG. 1 is a perspective view of the prosthesis which I use in accordance with the preferred embodiment of my improved procedure for repairing a sliding esophageal distal hernia.

Turning now to the drawings, FIG. 1 depicts the prosthetic device which I utilize in the preferred embodiment of my improved method for maintaining the reduction of an esophageal hiatal hernia. The prosthesis consists of a generally C-shaped cushion member 21, the inside dimensions of which generally correspond to the normal outside dimensions of the distal esophagus (reference character 17, FIG. 5). In a typical prosthesis, the inside dimensions will equal about 3.1 by 2.5 centimeters, although prosthetic devices having somewhat larger and somewhat smaller inside dimensions should be provided to the surgeon for use where the patient may have an esophagus somewhat larger or somewhat smaller than normal.

The outside dimensions of the prosthesis are sized to be substantially larger than the enlarged esophageal hiatus (reference character 12, FIG. 5), and in a typical prosthesis, the outside dimensions will equal about 6.0 by 7.0 centimeters. Obviously, these outside dimensions are also variable in accordance with the size of the enlarged esophageal hiatus of a particular patient.

Figure 2:
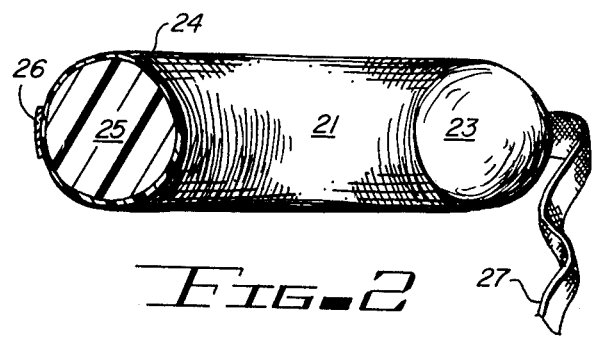
FIG. 2 is a sectional side view of the prosthesis of FIG. 1 taken along section line 2—2 thereof.
Figure 3:
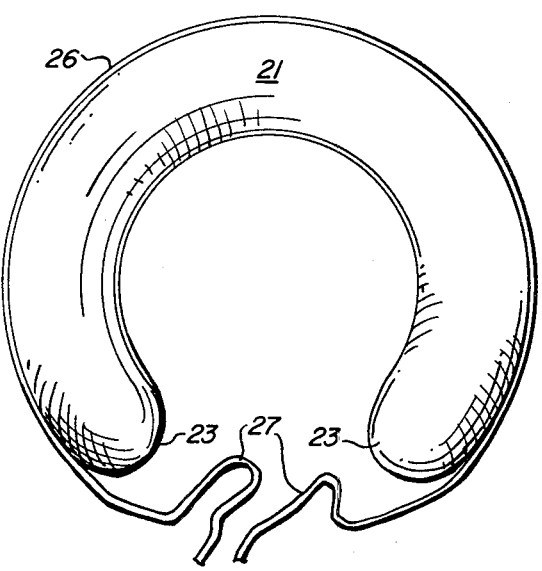
FIG. 3 is a top view of the prosthesis of FIG. 1.

In accordance with the prosthesis as shown in FIGS. 1–3, the cushion member has a generally circular cross-section and is of generally constant cross-sectional area along the length thereof. The prosthesis is preferably constructed by filling outer flexible integument 24 with a gel liquid 25 such that the entire cushion member 21 is deformable to permit adjustment of the spacing of the free ends 23 at a selected distance which will permit the normal expansion of the esophagus during swallowing. The precise materials of construction of the integument 24 and the filler 25 of the C-shaped cushion member 21 are not highly critical so long as they are compatible with body tissues, i.e., do not induce rejection or cause other body reaction. In the presently preferred embodiment of the invention, I employ a silicone elastomer shell filled with a highly cross linked silicone gel manufactured by Dow Chemical Company and sold under the trade name "Silastic". A tape 26, preferably siliconecoated Dacron, is secured to the C-shaped cushion member 21 around the outer periphery thereof and the free ends 27 of the tape extend substantially beyond the free ends 23 of the C-shaped cushion member 21 to a distance sufficient to allow the free ends 27 of the tape 26 to be tied together.

Preferably, the prosthesis is provided with a tantalum filled silicone strip 28 on tape 26 such that after implantation of the prosthesis, radiographic examination will reveal whether the prosthesis is in its proper operative position.

Figure 4:
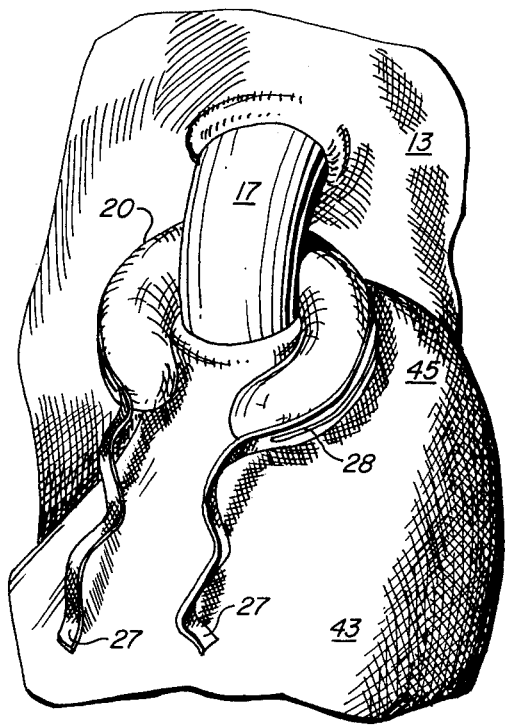
FIG. 4 is a perspective anatomical drawing illustrating the initial steps according to my method of reduction of the hiatal hernia.
Figure 5:
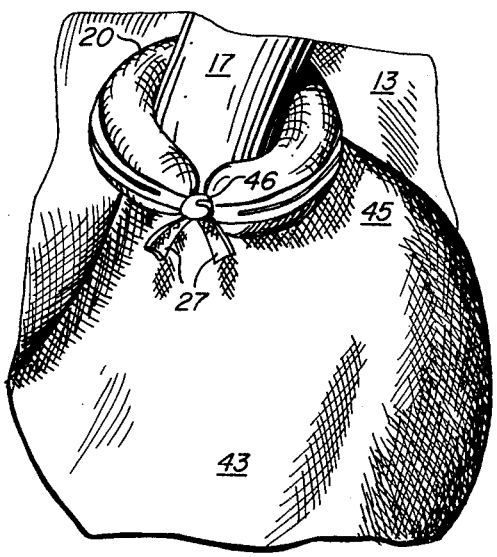
FIG. 5 is a perspective anatomical drawing illustrating the prosthesis of FIGS. 1-3 located in a proper operative position to prevent recurrence of the hiatal hernia.

The method of use of the prosthesis of FIGS. 1–3 is illustrated in FIGS. 4 and 5. My procedure consists of opening the abdominal cavity with an upper midline incision and exposing the area of the diaphragmatic hiatus by medially retracting the left lobe of the liver. The peritoneum and sac of the hiatal hernia 12 are then incised and the hernia 12 is reduced by retracting the stomach 43 intra-abdominally. As shown in FIG. 4, the prosthesis 20 of FIGS. 1–3 is then placed around the distal esophagus 17 immediately above the gastric fundus 45. FIG. 5 illustrates the prosthesis 20 in position after the free ends 27 of the tape 26 are anteriorly tied at 46 to locate the free ends 23 of the prosthesis 20 at the proper spacing and the tape end remnants are cut leaving about an inch of length. Suturing of the free ends to the stomach or to other anatomical structures is not required to maintain the prosthesis 20 in its proper operative position around the distal esophagus 17 between the gastric fundus 45 and the diaphragm 13.

The prosthesis shown in my earlier issued U.S. Pat. No. 3,875,928 has tapered ends and a larger sized center portion. In the proper operational position, the center portion of the tapered prosthesis is situated behind the distal esophagus 17 to increase the curvature of the esophagus. Increased curvature of the esophagus apparently tends to reduce gastro esophageal reflux. When the sutures binding the free ends of the Dacron tape to the stomach free themselves the tapered ends of the C-shaped cushion prosthesis tend to rotate to a position behind the esophagus 17 and above the gastric fundus 45. Since the size of the tapered ends of the prosthesis is insufficient to accentuate the curvature of the esophagus, the lessening of gastro esophageal reflux achieved when the tapered prosthesis also initially placed in the proper operative position is lost. In addition, after rotating to a position above the gastric fundus, the tapered ends tend to enter the hiatal hernia 12 and promote upward migration of the prosthesis through the diaphragmatic hiatus 12.

In contrast to the tapered prosthesis described in my earlier issued patent, the prosthesis herein illustrated in FIGS. 1–3 is of generally constant cross-sectional area along its entire length, i.e., the ends of the prosthesis are not substantially tapered. Consequently, even if the prosthesis rotates about the distal esophagus, the accentuation of the curvature of the esophagus 17 is maintained. Further, in the great majority of hiatal hernias, the consistent size of the present prosthesis along the length thereof eliminates upward migration of the prosthesis into and through the diaphragmatic hiatus. The prosthesis generally maintains the proper operative position between diaphragm 13 and stomach 43.

In sum, in the presently preferred embodiment of my improved method, the prosthesis need not be sutured in position to effectively maintain the reduction of a sliding esophageal hiatal hernia.

Having now described my invention and the use thereof in such clear, concise and exact terms as to enable those skilled in the art to understand the invention and practice it, and having identified the presently preferred embodiment of the invention,

I claim:

1. A method for maintaining the intra-abdominal reduction of a sliding esophageal hiatal hernia whereby extension of the gastric fundus into the thoracic cavity through an enlarged esophageal hiatal is prevented, said method comprising:

(a) positioning a generally C-shaped cushion prosthesis around the distal esophagus, the inside diameter of said prosthesis generally corresponding to the normal outside diameter of the distal esophagus and the outside diameter thereof being larger than said enlarged esophageal hiatus, said C-shaped member being deformable to permit adjustment of the spacing of the free ends thereof at a selected distance and having a generally constant cross-sectional area along the entire length thereof;

(b) adjusting said free ends of said prosthesis at a spacing to permit normal expansion of the esophagus during swallowing; and (c) fixing said free ends of said prosthesis in said adjusted position to maintain said C-shaped cushion prosthesis in operative position around the distal esophagus between the gastric fundus and the diaphragm and to maintain said adjusted spacing of said free ends, said prosthesis being maintained in said operative position free of any sutures interconnecting said prosthesis with an organ of the human body.

* * * * *